United States Patent [19]
Ito et al.

[11] Patent Number: 5,637,548
[45] Date of Patent: Jun. 10, 1997

[54] PREPARATION OF BIMETALLIC CATALYSTS FOR HYDRODECHLORINATION OF CHLORINATED HYDROCARBONS

[75] Inventors: Larry N. Ito; Mark E. Jones; Simon R. Bare, all of Midland, Mich.

[73] Assignee: The Dow Chemical Company, Midland, Mich.

[21] Appl. No.: 499,693

[22] Filed: Jul. 7, 1995

[51] Int. Cl.⁶ .............. B01J 37/00; B01J 23/58; B01J 23/72; C07C 1/00
[52] U.S. Cl. .............. 502/330; 502/331; 502/514; 585/733
[58] Field of Search .................. 502/330, 331, 502/514; 585/733, 820

[56] References Cited

FOREIGN PATENT DOCUMENTS

| 0459463 | 5/1991 | European Pat. Off. . |
| 0640574 | 8/1994 | European Pat. Off. . |
| 9407828 | 4/1994 | WIPO . |

Primary Examiner—Glenn A. Caldarola
Assistant Examiner—In Suk Bullock

[57] ABSTRACT

A process for preparing a bimetallic catalyst useful for the hydrodechlorination of chlorinated hydrocarbons, comprising impregnating a support with an active hydrogenating metal from a salt solution of the metal, recovering and drying the thus-impregnated support, reducing the impregnated support by exposure to hydrogen and oxidizing the active hydrogenating metal on said support to an oxidized state by exposure to an oxidizing environment, then impregnating the thus-treated support with a surface segregating metal from a salt solution thereof, aging the support/salt solution mixture over a period of time at an elevated temperature, and finally cooling, recovering and drying the catalyst before charging the same to a reactor for reduction or reduction and chloride source pretreatment and subsequent use.

11 Claims, No Drawings

5,637,548

PREPARATION OF BIMETALLIC CATALYSTS FOR HYDRODECHLORINATION OF CHLORINATED HYDROCARBONS

BACKGROUND

The present invention relates to processes for the hydrodechlorination of chlorinated hydrocarbons and to the catalysts employed therein, and more specifically relates in this broader aspect to methods of preparing these catalysts.

In the chlorofluorocarbon art, EP 0 459 463 A1 to Daikin Industries, Ltd. describes the preparation of 1-chloro-1,2,2-trifluoroethylene or 1,2,2,-trifluoroethylene, by reacting 1,1, 2-trichloro-1,2,2,-trlfluoroethane and hydrogen in the presence of a supported bimetallic catalyst comprising a "basic metal" (Pd, Rh or Ru) and an "additive metal" (Hg, Pb, Cd, Sn, In, Cu, Bi, Tl or Ag). The method shown for making these catalysts involves making a salt solution of an "additive" metal in water, adding to this solution a quantity of formalin (a solution of formaldehyde in water and methanol) and a supported "basic metal" catalyst in pellet or powder form, aging the mixture at 50 degrees Celsius for 2 to 3 hours, then drying the catalyst and pretreating with hydrogen at 300 to 400 degrees Celsius for 2 hours (all of the additive metals besides bismuth) or with oxygen at 300 degrees Celsius for the same 2 hours (where bismuth is the additive metal).

Outside of the chlorofluorocarbon art as such, however, a number of processes are described for converting a chlorinated hydrocarbon to a less-chlorinated hydrocarbon and hydrogen chloride via catalysts made by other methods, exemplary hydrodechlorination processes being those described in EP 015665 (converting 1,1,2-trichloroethane to ethylene or vinyl chloride), GB 1 400 529 (converting "hydrocarbon chlorides" to "chlorine-free hydrocarbons"), DD 235 630 A1 (converting 1,2-dichloropropane to propylene), U.S. Pat. Nos. 4,818,368, 4,882,037 and 4,923, 590 (the hydrogenation of halogenated hydrocarbons), CA 1 119 203 (converting perchloroethylene to trichloroethylene), DE 3 804 265 A1 (same) and U.S. Pat. No. 5,091,603 (same).

Commonly-assigned U.S. patent application Ser. No. 08/112,042, now abandoned (which has been published under the Patent Cooperation Treaty as WO 94/07828), and U.S. application Ser. No. 08/227,812, filed as a continuation-in-part of the '042 application and now allowed, U.S. Pat. No. 5,453,557, are of particular relevance or interest, and similarly describe processes for converting a chlorinated alkane, for example 1,2-dichloropropane to a corresponding less-chlorinated (including non-chlorinated) alkene (propylene for 1,2-dichloropropane) and hydrogen chloride. The catalysts described in the '812 application more particularly are preferably bimetallic catalysts of an active hydrogenating metal (inclusive of the preferred Group VIII metals such as platinum (as per the '042 application) and being inclusive also of chromium, tungsten and molybdenum) and of a surface segregating metal (preferably being a Group IB metal of copper, silver or gold, copper being especially preferred) on a support (which is preferably a carbon support). A most preferred catalyst from the '042 and '812 applications, which applications are incorporated herein by reference, is a bimetallic catalyst of platinum and copper on a commercially-available BPLF3 grade carbon from Calgon Carbon Corporation, Pittsburgh, Pa.

Methods described or exemplified for making this Pt/Cu bimetallic catalyst in the '042 and '812 applications essentially involve coimpregnation of the carbon support from a solution of platinum and copper salts (e.g., chloroplatinic acid and $CuCl_2$), air-drying under ambient conditions, and oven drying at an elevated temperature prior to reduction with hydrogen and/or pretreatment by exposure to a chloride source.

SUMMARY OF THE PRESENT INVENTION

The present invention is concerned with the discovery of a novel and improved method of fabricating the hydrodechlorination catalysts described in the '042 and '812 applications, wherein the amount of copper or other surface segregating metal in the supported active hydrogenating metal/surface segregating metal catalysts of the prior, commonly-assigned applications may be reduced with a corresponding reduction in the raw materials expense in making the catalyst, while realizing improved product yields over the catalyst's lifetime through reduced overall byproduct formation and while promising lower catalyst deactivation rates.

In this regard, it is believed that the active site in the most preferred Pt/Cu bimetallic catalysts for the conversion of 1,2-dichloropropane to propylene and hydrogen chloride comprises a platinum-rich metal alloy particle including small amounts of copper.

Significant excesses of copper have, however, been required in the coimpregnation methods employed to date in manufacturing the most preferred Pt/Cu hydrodechlorination catalysts, to achieve a sufficient concentration of copper in the alloy particles with platinum. This excess copper is highly dispersed on the favored carbon supports, and results in needless added catalyst expense while catalyzing the formation of unwanted by-products such as 2-chloropropane, as well as possibly serving as initiation sites for coking reactions to occur.

The present, inventive catalyst manufacturing method enables the elimination of these large excesses of copper or other surface segregating metal, by more highly selectively associating and alloying the copper with the platinum or selected other active hydrogenating metal.

This is accomplished through a series of steps, comprising:

impregnating a support with an active hydrogenating metal from a salt solution of the metal;

recovering and drying the thus-impregnated support;

reducing the impregnated support by exposure to hydrogen; and oxidizing the active hydrogenating metal on said support to an oxidized state by exposure to an oxidizing environment; then impregnating the thus-treated support with surface segregating metal from a salt solution thereof which optionally and preferably further comprises formalin, or wherein the salt is optionally and preferably a formate or chloroformate salt of the surface segregating metal;

aging the support/salt solution mixture over a period of time at an elevated temperature; then cooling, recovering and drying the catalyst for subsequent use according to the teachings of the '042 and '812 applications.

DETAILED DESCRIPTION OF PREFERRED EMBODIMENTS

The present inventive process of preparing the bimetallic catalysts of the commonly-assigned '042 and '812 applications is fundamentally similar in its preferred embodiments to the process used in the above-referenced EP 0 459 463 A1 application to Daikin Industries, Ltd. (which is incorporated herein by reference) for making a useful catalyst for the particular process disclosed therein. Consequently it is not considered necessary to describe this process in exhaustive detail except to note the necessity (not addressed in the Daikin Industries application) of preoxidizing the platinum, iridium or other active hydrogenating metal on the support before incorporation of the Group IB surface segregating metal and exposure to formalin in the manner of the Daikin Industries application, and to further note the possibility of incorporating the Group IB surface segregating metal via a Group IB formate or chloroformate salt, e.g., copper formate or copper chloroformate, in lieu o a formalin treatment, with the use of formalin being preferred in the context of the present invention to the use of a formate or chloroformate salt.

The conditions which are necessary to oxidize the active hydrogenating metal to an extent whereby the improvements and advantages of the present invention may be realized, will depend on the particular hydrogenating metal employed. For the preferred Group VIII hydrogenating metals, for example, oxidation in air at elevated temperatures of about 50 degrees Celsius and greater is expected to be sufficient for rhodium and palladium, while for platinum (most preferred as the active hydrogenating metal, in combination with copper as the surface segregating metal) and iridium the oxidation will preferably be by exposure to oxygen at temperatures of about 300 degrees Celsius and greater.

It is also worthwhile to note that as observed in the '812 application, chloride pretreatment of the coimpregnated catalysts of that application is successful in reducing initial propane make, ostensibly also through increasing the efficiency with which the copper atoms present are alloyed with the platinum present. Consequently, it may be desirable to utilize the present preparation method as well as reduction and chloride source pretreatment of the catalyst when charged to the reactor for use, to most effectively associate the copper with the platinum on the catalyst support and thereby reduce initial propane make without also increasing 2-chloropropane production or compromising the conversion as would conventionally result from the employment of greater copper levels to reduce propane make.

The present invention is more particularly illustrated by the Examples which follow:

ILLUSTRATIVE EXAMPLES

For the examples which follow, several catalysts were made including platinum and copper on the same Calgon BPLF3 activated carbon support (6 by 16 mesh, Calgon Carbon Corporation, Pittsburgh, Pa.). These were each evaluated for their effectiveness and utility in catalyzing the gas phase reaction of hydrogen and 1,2-dichloropropane (or PDC) to produce propylene and hydrogen chloride, in the manner of the commonly-assigned '042 and '812 applications, by the conversion of PDC to products (100 minus the mol percent of PDC in the test reactor effluent, excluding HCl and unreacted hydrogen) and by the selectivity shown to production of propane, propylene and 2-chloropropane (mols of component divided by mols PDC converted, times 100).

For each example, PDC was converted to the reaction products by following hydrogen and PDC in the gas phase over a given catalyst to be evaluated (1.2 cubic centimeters between 3 mm glass beads). Liquid PDC was pumped via a piston pump through 1/16th inch (O.D.) nickel tubing to a Monel™ alloy (Huntington Alloys, Inco Alloys International, Inc.) gas sample cylinder packed with glass beads (unless specifically noted, all fittings and tubing were of Monel™ alloy). The 1/16th inch tubing extended to the center of the sample cylinder, with the sample cylinder being heated to a vaporization temperature of 110 degrees Celsius by electrical heat tracing. A thermocouple was used to monitor the skin temperature of the sample cylinder.

The flow of the hydrogen feed stream was controlled by a pre-calibrated mass flow controller to correspond to a hydrogen to PDC molar feed ratio of 1.0 to 1. The desired flow of hydrogen was passed through the heated sample cylinder, where mixing of the gaseous PDC and hydrogen occurred. The mixed gases were then passed into a charged Hastelloy™ C tubular reactor (0.50 in. O.D., 8 inches in length) heated by ceramic lined electric elements to the desired reaction temperature of 235 degrees Celsius, and maintained at a pressure of 75 pounds per square inch, gauge. The residence time in each run was 9.0 seconds, and the runs were maintained for 100 hours on stream.

The effluent from the reactor was passed to a gas sampling valve, which provided gaseous aliquots for online gas chromatographic analysis in a Hewlett-Packard Model 5890 Series II gas chromatograph, equipped with 30 meter by 0.53 millimeter (I.D.) 100 percent methyl silicone/fused silica and 30 meter by 0.53 millimeter (I.D.) porous polymer-lined fused silica columns and a flame ionization detector.

Example 1

For each of the examples herein (with the exception of Comparative Example 1 below), the catalyst in question was made by first preparing an aqueous chloroplatinic acid ($H_2PtCl_6$) stock solution of 0.3592 grams of $H_2PtCl_6.H_2O$ (J. T. Baker Inc., Baker Analyzed Grade, 37.6 percent Pt) in 33.4 ml of deionized and distilled water (18.2 megohm resistance). Calgon BPLF3 activated carbon, 6×16 mesh, was added at 27.0 grams to the flask containing the aqueous chloroplatinic acid solution. The flask was agitated rapidly in a manner such that the carbon carrier was evenly coated with the solution, after which the Pt-impregnated carrier was air dried in an evaporating dish at ambient temperature for 18 hours, and then further air dried in an oven at 120 degrees Celsius for 2 hours.

In this example, 2.00 grams of this 0.50 percent Pt on carbon material was further dried in a quartz reactor at 350 degrees Celsius under flowing helium for 2 hours, then reduced at 350 degrees Celsius under flowing hydrogen for another 2 hours. After purging the reactor with helium at this temperature, the catalyst was oxidized under 2 pct. oxygen in helium for 5 minutes (at 350 deg. Celsius) and then cooled to ambient temperature under this atmosphere. Thereafter, 4.9 milligrams $CuCl_2$ (Aldrich Chemical Company Inc., 99,999 percent purity) were dissolved in 7.5 ml of distilled, deionized water to which the Pt/C material was added, to provide a catalyst composed of 0.5 weight percent of platinum and 0.1 weight percent of copper on an elemental basis. Formalin was added at 0.5 grams in a dropwise manner to the mixture, and the mixture heated to 50 degrees Celsius for 5 hours. The catalyst was cooled to room temperature, filtered and dried at ambient temperature in air before being charged to the reactor, dried under nitrogen at 235 degrees Celsius for 2 hours and then reduced under hydrogen for an hour at this temperature.

The results from this catalyst preparation showed a PDC conversion of 57.0 percent, a selectivity to propylene of 88.5 percent, a propane selectivity of 4.7 percent and a 2-chloropropane selectivity of 6.7 percent. These results are shown in Table 1, along with results from catalysts A-D prepared by similar processes and also including 0.5 weight percent of platinum with 0.1 weight percent of copper on an elemental basis, but omitting one or more of the steps of the present invention and of the run just described:

TABLE 1

| Catalyst | PDC Conv. (%) | $C_3H_6$ Sel. (%) | $C_3H_8$ Sel. (%) | 2-CPa[a] Sel. (%) |
| --- | --- | --- | --- | --- |
| Ex. 1 | 57.0 | 88.5 | 4.7 | 6.7 |
| A | 61.4 | 29.5 | 46.0 | 24.1 |
| B | 54.9 | 29.0 | 51.9 | 16.7 |
| C | 63.5 | 21.5 | 54.1 | 22.8 |
| D | 58.3 | 26.8 | 70.2 | 2.6 |

Catalyst A: Two (2.00) grams of the Pt/C material were dried in a quartz reactor at 350 degrees Celsius under flowing helium for 2 hours, and then reduced at this temperature under flowing hydrogen for 2 additional hours. The material was then cooled (without being oxidized) to ambient temperature, under this atmosphere. $CuCl_2$ was then added at 4.9 milligrams to 7.5 ml of water, and dissolved. The Pt/C material was added to the $CuCl_2$ solution with 0.5 grams of formalin, added dropwise. The mixture was heated to 50 degrees Celsius for 5 hours, then the mixture was cooled, filtered to recover the catalyst and the catalyst dried at ambient temperature in air.

Catalyst B: Two (2.00) grams of the Pt/C material were dried again at 350 degrees Celsius under flowing helium for 2 hours, and then reduced at this temperature under flowing hydrogen for 2 hours before being cooled to ambient temperature under this atmosphere. 4.9 milligrams of $CuCl_2$ were dissolved in 7.5 ml of water, and the Pt/C material added to this solution along with 0.5 grams of formalin added dropwise. The mixture was heated to 50 degrees Celsius for 10 hours rather than 5 hours, the mixture was cooled to room temperature, filtered to recover the catalyst and the catalyst air-dried at ambient temperatures.

Catalyst C: Two (2.00) grams of the Pt/C material were dried at 350 degrees Celsius under flowing helium for 2 hours, and then reduced at this temperature under flowing hydrogen for 2 hours before being cooled to ambient temperature under this atmosphere. 4.9 milligrams of $CuCl_2$ were dissolved in 7.5 ml of water, and the Pt/C material added to this solution along with 0.5 grams of formalin added dropwise. The mixture was heated to 90 degrees Celsius for 5 hours, the mixture was cooled to room temperature, filtered to recover the catalyst and the catalyst air-dried at ambient temperatures.

Catalyst D: Two (2.00) grams of the Pt/C material were dried at 350 degrees Celsius under flowing helium for 2 hours, and then reduced at this temperature under flowing hydrogen for 2 hours before being cooled to ambient temperature under this atmosphere. 4.9 milligrams of $CuCl_2$ were dissolved in 15.0 ml of water, and the Pt/C material added to this solution along with 0.5 grams of formalin added dropwise. The mixture was heated to 50 degrees Celsius for 5 hours, the mixture was cooled to room temperature, filtered to recover the catalyst and the catalyst air-dried at ambient temperatures.

Example 2

Two (2.00) grams of the 0.50 percent Pt on carbon material from Example 1 were dried at 350 degrees Celsius in a quartz reactor under flowing helium for 2 hours, then reduced at 350 degrees Celsius under flowing hydrogen for another 2 hours. After purging the reactor with helium at this temperature, the catalyst was oxidized under 2 pct. oxygen in helium for 5 minutes (at 350 deg. Celsius) and then cooled to ambient temperature under this atmosphere. Thereafter, 4.9 milligrams $CuCl_2$ (Aldrich Chemical Company Inc., 99.999 percent purity) were dissolved in 7.5 ml of distilled, deionized water, the Pt/C material alone was added and the mixture heated to 50 degrees Celsius for 5 hours. The catalyst was cooled to room temperature, filtered and dried at ambient temperature in air before being charged to the reactor and evaluated. The PDC conversion was found to be 59.5 percent, the propylene selectivity was 66.3 percent, the propane selectivity was 28.2 percent and the selectivity to 2-chloropropane was 4.7 percent.

Example 3

Two (2.00) grams of the 0.50 percent Pt on carbon material from Example 1 were dried at 350 degrees Celsius in a quartz reactor under flowing helium for 2 hours, then reduced at 350 degrees Celsius under flowing hydrogen for another 2 hours. After purging the reactor with helium at this temperature, the catalyst was oxidized under 2 pct. oxygen in helium for 5 minutes (at 350 deg. Celsius) and then cooled to ambient temperature under this atmosphere. Thereafter, 16.1 milligrams of $Cu(OCHO)_2$ were dissolved in 7.5 ml of distilled, deionized water, the Pt/C material was added and the mixture heated to 50 degrees Celsius for 5 hours. The catalyst, comprising 0.5 weight percent of platinum and 0.2 weight percent of copper on an elemental basis rather than the 0.1 weight percent of copper found in the catalysts of Examples 1 and 2, was cooled to room temperature, filtered and dried at ambient temperature in air before being charged to the reactor and evaluated. The PDC conversion was found to be 45.2 percent the propylene selectivity was 85.7 percent, the propane selectivity was 10.7 percent and the selectivity to 2-chloropropane was 2.5 percent.

Example 4

Two (2.00) grams of the 0.50 percent Pt on carbon material from Example 1 were dried at 350 degrees Celsius in a quartz reactor under flowing helium for 2 hours, then reduced at 350 degrees Celsius under flowing hydrogen for another 2 hours. After purging the reactor with helium at this temperature the catalyst was oxidized under 2 pct. oxygen in helium for 5 minutes (at 350 deg. Celsius) and then cooled to ambient temperature under this atmosphere. Thereafter, 9.8 milligrams $CuCl_2$ (Aldrich Chemical Company Inc., 99.999 percent purity) were dissolved in 7.5 ml of distilled, deionized water, the Pt/C material alone was added and the mixture heated to 50 degrees Celsius for 5 hours. The catalyst (including 0.5 weight percent of platinum and 0.2 weight percent of copper on an elemental basis, in common with Example 3) was cooled to room temperature, filtered and dried at ambient temperature in air before being charged to the reactor and evaluated. The PDC conversion was found to be 47.8 percent, the propylene selectivity was 90.9 percent, the propane selectivity was 1.3 percent and the selectivity to 2-chloropropane was 7.3 percent.

Examples 1, 3 and 4 together suggest that formalin treatment is probably preferable to use of a formate or chloroformate salt of a Group IB or other surface segregating metal in preparation of the contemplated catalysts, and also suggest that, in considering the PDC conversions and product selectivities observed with these Examples as a whole, the optimum level of copper to go with the 0.5 weight percent of platinum in the Pt/Cu catalysts made in these Examples should probably be between the 0.1 and 0.2 weight percent loadings exemplified herein.

Comparative Example 1

A catalyst including 0.5 weight percent of platinum and 0.9 percent of copper on an elemental basis on the Calgon BPLF3 activated carbon of previous examples was made for comparison according to the teachings of the '042 and '812 applications, by a coimpregnation technique. An aqueous chloroplatinic acid stock solution was prepared initially by dissolving 3.179 grams of $H_2PtCl_6 \cdot 6H_2O$ in 100.00 ml of deionized, distilled water. Into a 250 ml Erlenmeyer flask were then placed 0.381 grams of $CuCl_2$, and 8.305 grams of the stock solution were added with swirling to provide a homogeneous solution. The solution was diluted with 42.64 grams o water, and 20.02 grams o the BPLF3 carbon were added with swirling to evenly coat the carbon support with the solution. The coated support was recovered by filtration, air dried in an evaporating dish at ambient temperature for 18 hours and then further air dried in an oven at 120 degrees Celsius for 2 hours, before being charged and evaluated as in previous examples.

The resulting PDC conversion was 56.7 percent, with the selectivity to propylene being 86.1 percent, the selectivity to propane being 0.55 percent and the 2-chloropropane selectivity being 13.4 percent. These figures can be compared again to those seen with Examples 1 and 4:

TABLE 2

| Catalyst | PDC Conv. (%) | $C_3H_6$ Sel. (%) | $C_3H_8$ Sel. (%) | 2-CPa$^{(a)}$ Sel. (%) |
|---|---|---|---|---|
| Ex. 1 (0.5 Pt/0.1 Cu) | 57.0 | 88.5 | 4.7 | 6.7 |
| Ex. 4 (0.5 Pt/0.2 Cu) | 47.8 | 90.9 | 1.3 | 7.3 |
| Comp. Ex. 1 (0.5 Pt/0.9 Cu) | 56.7 | 86.1 | 0.55 | 13.4 |

Those skilled in the art will appreciate that while preferred embodiments have been described and exemplified herein, and more particularly, while the process of the present invention has been illustrated with respect to the most preferred Pt/Cu, carbon-supported catalysts of the '042 and '812 applications the improvements indicated herein should be achievable also with other catalyst embodiments embraced within these applications through routine optimization and experimentation.

What is claimed is:

1. A process for preparing a bimetallic catalyst useful for the hydrodechlorination of chlorinated hydrocarbons, comprising:

impregnating a support with an active hydrogenating metal from a salt solution of the metal;

recovering and drying the thus-impregnated support;

reducing the impregnated support by exposure to hydrogen; and oxidizing the active hydrogenating metal on said support to an oxidized state by exposure to an oxidizing environment; then impregnating the thus-treated support with a surface segregating metal from a salt solution thereof;

aging the support/salt solution mixture over a period of time at an elevated temperature; then cooling, recovering and drying the catalyst.

2. A process as defined in claim 1, wherein the salt solution of the surface segregating metal further comprises formalin, or wherein the surface segregating metal salt is a formate or chloroformate salt of the surface segregating metal.

3. A process as defined in claim 2, wherein the surface segregating metal salt solution further comprises formalin.

4. A process as defined in claim 1, wherein the active hydrogenating metal is platinum or iridium and wherein the platinum or iridium is oxidized by exposure to oxygen at elevated temperatures of about 300 degrees Celsius or greater.

5. A process as defined in claim 2, wherein the active hydrogenating metal is platinum or iridium and wherein the platinum or iridium is oxidized by exposure to oxygen at elevated temperatures of about 300 degrees Celsius or greater.

6. A process as defined in claim 3, wherein the active hydrogenating metal is platinum or iridium and wherein the platinum or iridium is oxidized by exposure to oxygen at elevated temperatures of about 300 degrees Celsius or greater.

7. A process as defined in claim 1, wherein the active hydrogenating metal is a Group VIII metal, and wherein the surface segregating metal is a Group IB metal.

8. A process as defined in claim 7, wherein the Group VIII metal is platinum and wherein the Group IB surface segregating metal is copper.

9. A process as defined in claim 8, wherein the platinum is oxidized by exposure to oxygen at elevated temperatures of about 300 degrees Celsius or greater.

10. A process as defined in claim 3, wherein the active hydrogenating metal is platinum and wherein the surface segregating metal is copper.

11. A process as defined in claim 10, wherein the platinum is oxidized by exposure to oxygen at elevated temperatures of about 300 degrees Celsius or greater.

* * * * *